(12) United States Patent
Perricone

(10) Patent No.: US 6,437,004 B1
(45) Date of Patent: Aug. 20, 2002

(54) TREATMENT OF SKIN DAMAGE USING OLIVE OIL POLYPHENOLS

(76) Inventor: Nicholas V. Perricone, 27 Coginchaug Ct., Guilford, CT (US) 06437

( * ) Notice: Subject to any disclaimer, the term of this patent is extended or adjusted under 35 U.S.C. 154(b) by 0 days.

(21) Appl. No.: 09/763,333

(22) PCT Filed: Jun. 23, 2000

(86) PCT No.: PCT/US00/17488

§ 371 (c)(1),
(2), (4) Date: May 7, 2001

(87) PCT Pub. No.: WO01/76579

PCT Pub. Date: Oct. 18, 2001

Related U.S. Application Data

(60) Provisional application No. 60/195,171, filed on Apr. 6, 2000.

(51) Int. Cl.[7] ...................... A61K 31/045; A61K 31/05; A61K 31/335; A61K 31/35
(52) U.S. Cl. .......................... 514/738; 514/731; 514/451; 514/452
(58) Field of Search ................................ 514/731, 452, 514/738, 451

(56) References Cited

U.S. PATENT DOCUMENTS 5,719,129 A 2/1998 Andary et al.
6,162,480 A * 12/2000 van Buuren et al. ...... 426/330.6

FOREIGN PATENT DOCUMENTS

| FR | 2652086 | 9/1989 |
|---|---|---|
| JP | 8151319 | 11/1994 |
| JP | 08119825 A | * 9/1996 |

OTHER PUBLICATIONS

Aruoma, O.I., et al., Oxygen '99, S31, abstract 57.
Amari, and Maramaldi, SOFW–Journal 125: 30–32, Aug. 1999.
Dubertret, L., Skin News 6 Editorial, May 1999.
Fehri, B., et al., Boll. Chim. Farmaceutico 135: 42–49, 1996.
Ibbotson, S.H., et al., J. Invest. Dermatol. 112: 933–938, 1999.
Kiritsakis, A.K., J. Amer. Oil Chem. Soc. 75: 673–681, 1998.
Papadopoulos, G., and Boskou, D., J. Amer. Oil Chem. Soc. 68: 669–671 (1991).
Papadopoulos, G., et al., Food Flavors, Ingredients and Composition, Elsevier Science Pub., pp. 321–326, 1993.
Tsimidou, M., et al., Food Chemistry 45: 141–144, 1992.
Visioli, F., et al., Biochem. Biophys. Res. Comun. 247: 60–64 (1998).

* cited by examiner

*Primary Examiner*—Theodore J. Criares
*Assistant Examiner*—Jennifer Kim
(74) *Attorney, Agent, or Firm*—Mary M. Krinsky

(57) ABSTRACT

Free radical-scavenging olive oil polyphenols are topically applied to treat skin damage, such as contact dermatitis (particularly diaper area dermatitis), atopic dermatitis, xerosis, eczema (including severe hand and foot eczema), rosacea, seborrhea, psoriasis, thermal and radiation burns, other types of skin inflammation, and aging. Typical compositions contain from about 0.25% to about 10% of a polyphenol preparation obtained from olive oil.

20 Claims, No Drawings

TREATMENT OF SKIN DAMAGE USING OLIVE OIL POLYPHENOLS

RELATED APPLICATION DATA

This application claims priority benefit of U.S. Ser. No. 60/195,171 filed Apr. 6, 2000 and of PCT/US00/17488 filed Jun. 23, 2000.

BACKGROUND OF THE INVENTION

1. Field of the Invention

This invention relates to the topical application of free radical-scavenging olive oil phenols such as hydroxytyrosol and oleuropein for the treatment of acute and chronic skin damage. Therapies according to the invention are particularly efficacious for treating a variety of skin conditions including contact dermatitis (particularly diaper area dermatitis), atopic dermatitis, xerosis, eczema, rosacea, seborrhea, psoriasis, thermal and radiation burns, other types of skin inflammation, and the tissue degerative effects of aging.

2. Description of Related Art

Skin inflammation and aging are closely related phenomena. So similar are the processes involved with both, that aging is sometimes described dermatologically as a chronic low grade inflammatory condition. In acute inflammation, there is typically a respiratory burst of neutrophil activity that initiates cascades that typically involve a change in the oxidation state of the cell. Acute inflammation is also characterized by mast cell degranulation wherein serotonin is produced, which acts as a signal transduction factor. Following that, excited oxygen species are generated, e.g., superoxide anion, and these damage the lipid-rich membranes and activate the chemical mediators of proinflammation and inflammation.

Alteration in the redox state of the cell activates transcription factors such as NFκB as well as AP1, which then causes production of proinflammation mediators. These mediators, such as TFα and various interleukins, cause a burst of cytokines. Arachadonic acid is released, which is oxidized to biologically active mediators. When arachadonic acid is oxidized via the cyclooxygenase or lipoxygenase pathways, for example, prostaglandins, leukotrines, and hyroxyeicosatetraenoic acid (HETE) are produced, which cause erythma, edema, and free radical production. Transcription factors such as NFκB and AP1 alter DNA expression in the cell and produce cytokines and proteinases such as collagenase.

Similar metabolic events are observed in skin aging. Cell age is due in part to free radical damage, which takes place mostly within the cell membrane. The cell membrane is most susceptible to attack by free radicals because of its dense molecular structure largely comprising lipids and lipoproteins, which are easily oxidized by reactive oxygen species. In skin, reactive oxygen species such as singlet oxygen, the superoxide anion, and hydroxyl radicals, as well as other free radicals, are generated in normal metabolism, as well as through ultraviolet sun exposure, other forms of radiation, other environmental factors such as pollution or exposure to chemicals in the home or workplace, and the like, active in the arachidonic acid cascade. As in inflammation, free radicals activate chemical mediators that produce prostaglandins and/or leukotrines.

The body contains an endogenous antioxidant defense system made up of antioxidants such as vitamins C and E, glutathione, and enzymes, e.g., superoxide dismutase. When metabolism increases or the body is subjected to other stress such as infection, extreme exercise, radiation (ionizing and non-ionizing), or chemicals, the endogenous antioxidant systems are overwhelmed, and free radical damage takes place. Over the years, the cell membrane continually receives damage from reactive oxygen species and other free radicals, resulting in cross-linkage or cleavage or proteins and lipoprotins, and oxidation of membrane lipids and lipoproteins. Damage to the cell membrane can result in myriad changes including loss of cell permeability, increased intercellular ionic concentration, and decreased cellular capacity to excrete or detoxify waste products. As the intercellular ionic concentration of potassium increases, colloid density increases and m-RNA and protein synthesis are hampered, resulting in decreased cellular repair. Some cells become so dehydrated they cannot function at all.

In skin aging, the regularity of tissue structure is lost. Individual cells enlarge, but the total number of cells decreases approximately 30%. Intercellular collagen increases, and the proportion of soluble collagen decreases. Cross-linking between long-chain collagen macromolecules occurs. Elastin loses its discrete structure and elasticity, and has an increased calcium content. The dermis microscars and diminishes.

Sunlight and chemical exposure wreaks far greater destruction on the skin than time itself, and intensifies and augments the aging process. There is substantial evidence that ultraviolet radiation induces the formation of reactive oxygen species which are implicated as toxic intermediates in the pathogenesis of photoaging (Ibbotson, S. H., et al., *J. Investig. Derm.* 112: 933–938 (1999)).

Activation of transcription factors such as AP1 causes gene expression of collagenases which cause further damage. Free radical damage to the surface of the skin from sun and chemical exposure is manifested as lines, mottling, discoloration, precancers and cancers. Aging of both skin and other tissues is, in part, the result of constant free radical damage to cell membranes, leading to decreased cell function. This results in accumulation of waste products in the cells, such as lipofuscin; increase in the potassium content of the cells, which results in dehydration of the cells; and decreased production of messenger RNA and proteins.

Early suggestions for dealing with aging effects in skin were predominantly aimed at lubrications and emollients through use of topical compositions containing soothing agents, e.g., as exemplified by commercial hand lotion products and the like. More recently, attention has been directed to agents which address the underlying processes involved in skin damage, such as the free radical generation processes. In this regard, investigations have been made with respect to the antioxidants vitamin E and vitamin C to quench free radicals on the surface of the skin and to protect lipid membranes intracellularly (Wilson, R., *Drug and Cosmetic Industry*, 32–34, 38, and 68, August 1992).

It would be desirable to have alternative topical compositions for skin damage, particularly compositions that are efficient in free radical scavenging in membranes.

BRIEF SUMMARY OF THE INVENTION

It is an objective of the invention to provide new compositions and methods for the treatment of skin damage, such as atopic dermatitis, contact dermatitis (particularly diaper area dermatitis), xerosis, eczema, rosacea, seborrhea, psoriasis, thermal and radiation burns, other types of skin inflammation, and aging.

These and other objectives of the invention are accomplished by the present invention, which provides methods and compositions containing free radical-scavenging olive oil polyphenols, which is topically applied to exposed or affected skin areas, primarily for the treatment but also for the prevention of skin damage, often in association with a dermatologically acceptable carrier. The amount of olive oil polyphenols necessary to treat damaged skin is not fixed per se, and necessarily is dependent upon the concentration and type of polyphenol in the dermatological composition, the user's skin type, and the severity, extent, and nature of the dermatological problem treated. In some typical embodiments, the composition contains from about 0.25% to about 10 weight %, more narrowly from about 1% to about 5 weight %, polyphenol. In one embodiment, about 2% to about 3% polyphenol is employed.

DETAILED DESCRIPTION OF THE INVENTION

In the practice of the invention, at least one olive oil polyphenol is used to treat skin damage when topically applied in effective amounts.

Any synthetic or natural olive oil polyphenol preparation may be employed in compositions of the invention. Natural preparations are preferred because they exhibit desirable physical characteristics and are both economical and nontoxic. By "polyphenol" is meant any polyphenol that scavenges free radicals and exhibits antioxidant activity. Preferred polyphenols bear two phenol groups in an ortho position, such as hydroxytyrosol (3,4-dihydroxyphenylethanol) and oleuropein found in high quality virgin olive oil. A typical polyphenol preparation is virgin olive oil harvested from a cultivar producing relatively high polyphenolic quantities, e.g., in the order of 800 mg/Kg of these "minor components", harvested from trees planted in soil and/or grown in climatic conditions, and/or obtained from oil produced and stored under conditions favoring a higher-than-average polyphenolic component, or polyphenolic-containing fractions of these oils such as fractions enriched with non-saponifiable natural olive oil materials. Polyphenols are part of the so-called "polar fraction" of virgin olive oil, which is usually obtained by extraction with methanol: water systems (Tsimidou, M., et al., *Food Chemistry* 45: 141–144 (1992)). Many of these phenol fraction preparations contain other o-diphenols such as protocatechuic acid, caffeic acid, and syringic acid as well as hydroxytyrosol (Papadopoulos, G., and Boskou, D., *J. Amer. Oil Chem. Soc.* 68: 669–671 (1991)).

Alternate embodiments employ olive oil enriched with oleuropein and/or hydroxytyrosol, or enriched with a polyphenolic-containing olive oil fraction. Other embodiments utilize either oleuropein or hydroxytyrosol or a mixture thereof, with polyphenols synthesized or obtained commercially. Preparations have been previously described and tested for their free-radical testing properties; see, for example, Visioli, F., et al., *Biochem. Biophys. Res. Com.* 247: 60–64 (1998), Papadopoulos and Boskou, cited above, and the references cited therein.

Free-radical scavenging olive oil polyphenols are fat-soluble. Therefore, polyphenol preparations, especially those using olive oil as a carrier for the poly-phenol active ingredient, can be applied neat to skin tissue. It is an advantage of the invention that the active compound is fatty so that it physically contributes to the lubrication of affected skin areas to which it is applied. It is another important advantage of the invention that preferred compositions contain natural, nontoxic materials as active ingredients.

However, only effective amounts of polyphenols are needed to treat skin damage, so generally topical application to exposed or affected skin sites is accomplished in association with a carrier, and particularly one in which the polyphenol active ingredient or olive oil containing it is soluble per se or is effectively solubilized (e.g., as an emulsion or microemulsion). Where employed, the carrier is inert in the sense of not bringing about a deactivation or oxidation of the polyphenol, and in the sense of not bringing about any adverse effect on the skin areas to which it is applied. In one preferred practice of the invention, polyphenol is applied in admixture with a dermatologically acceptable carrier or vehicle (e.g., as a lotion, cream, ointment, soap, stick, or the like) so as to facilitate topical application and, in some cases, provide additional therapeutic effects as might be brought about, e.g., by moisturizing of the affected skin or mucosal areas. While the polyphenol carrier for dermatological compositions can consist of a relatively simple solvent or dispersant such as water, it is generally preferred that the carrier comprise a composition more conducive to topical application, and particularly one which will form a film or layer on the skin to which it is applied so as to localize the application and provide some resistance to washing off by immersion in water or by perspiration and/or aid in the percutaneous delivery of the active agent. Many preparations are known in the art, and include lotions containing oils and/or alcohols and emollients such as olive oil, hydrocarbon oils and waxes, silicone oils, other vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophilic colloids. One preferred embodiment is an oil-in-water cream. Such compositions are referred to herein as dermally or dermatologically acceptable carriers.

Suitable carriers include water, alcohols, oils and the like, chosen for their ability to dissolve or disperse polyphenol and any other ingredients used in the treatment. Generally, even low concentrations of active ingredients in a carrier are suitable, depending upon the application regimen and adjunct ingredients employed. Many embodiments contain from about 0.1% to about 10% by weight, more narrowly from about 0.25% to about 5% to 7% by weight, polyphenol. Chronic conditions typically require a lower concentration of active polyphenol ingredient than to acute conditions. As a practical matter, however, to avoid the need for repeated application, it is desirable that the topically applied composition (i.e., polyphenol plus carrier) be formulated to contain at least about 1% by weight polyphenol, and many embodiments contain more than 1 weight % polyphenol. One efficacious embodiment contains from about 2% to about 5% by weight polyphenol.

Generally in the practice of methods of the invention, the composition is topically applied to the affected skin areas in a predetermined or as-needed regimen either at intervals by application of a lotion or the like, it generally being the case that gradual improvement is noted with each successive application. Insofar as has been determined based upon clinical studies to date, no adverse side effects are encountered.

Some embodiments of this invention contain at least one other adjunct ingredient in addition to polyphenol. Adjunct ingredients include, but are not limited to, α-hydroxy acids and fatty acid esters of ascorbic acid. Many embodiments employ more than one adjunct ingredient.

As used herein, the term "α-hydroxy acid" has reference to and encompasses the general class of organic compounds containing at least one hydroxy group and at least one carboxyl group, and wherein at least one hydroxyl group is located on the α-carbon atom. Typically, the compounds are organic acids having at least one carboxylic acid group and at least one hydroxyl group on the α-carbon atom, and may contain other functional groups including additional hydroxyl and carboxylic acid moieties. Preferred α-hydroxy acids and/or α-hydroxy acid derivatives are less bulky structurally so that they penetrate the skin well, and thus have a backbone of from one to three carbon atoms such as those set out in U.S. Pat. No. 5,965,618 at column 6 lines 4 to 29. Where employed, glycolic and/or lactic acid or their derivatives are preferred; glycolic acid is especially efficacious.

Fat-soluble fatty acid esters of ascorbic acid (vitamin C) is employed as an adjunct ingredient in other embodiments, alone or in combination with α-hydroxy acids. The more oxidation-resistant saturated fatty acid esters of ascorbic acid are preferred, including, but not limited to, ascorbyl laurate, ascorbyl myristate, ascorbyl palmitate, ascorbyl stearate, and ascorbyl behenate. Ascorbyl palmitate is used in one embodiment. As denoted herein, where fatty acid esters are described, e.g., ascorbyl stearate, compositions having predominantly that ester, e.g., predominantly stearate, are included. The esters may be prepared using hydrogenated oils or fats, or fractions thereof, and contain small amounts of another ester. Ascorbyl stearate prepared using canola, for example, commonly contain about 4% ascorbyl palmitate. It is an advantage of the invention that where fatty acid esters of ascorbic acid are employed as an adjunct ingredient, they help stabilize the polyphenol in the composition.

While not wishing to be bound to any theory, it is possible that polyphenol is efficacious in the treatment of skin damage because it is fat-soluble and readily disperses in cell membranes and other cellular components. Polyphenols readily penetrate skin. They are also active antioxidants that has been shown to scavenge superoxide radicals and inhibit neutrophilic respiratory bursts (Visioli, F., et al., cited above). Polyphenols act as free radical scavengers and neutralizers, and prevent the cross-linking of cell membranes that is often seen in its post-inflanmmatory phases. By the same token, polyphenol modulation of free radicals and other oxidative species appears to affect gene expression, including expression of nuclear factor κ-B (NF-κB), nitric oxide synthetase and other mediators at all stages of proinflammation and inflammation. Polyphenolic alteration of lipid peroxidation, protein cross-linking, growth factor stimulation, and membrane permeability may explain its negative effect on the symptoms of inflamed and aging skin.

When skin is inflamed from ultraviolet radiation, irritants, trauma, and other reasons, phospholipase-A-2 produces arachidonic acid from the phospholipid-rich membranes of the cell, resulting in the production of metabolites. We now know that stabilization of the cell membrane can inhibit the inflammatory cascade, therefore preventing the inflammatory response. It is also now known that arachidonic acid has a direct toxic effect on the mitochondria, resulting in the uncoupling of oxidative phosphorylation, resulting in free radical damage to the mitochondrial membrane, Free radical-scavenging olive oil polyphenols appear to intersperse in the cell membrane, stabilizing the membrane, and, at the same time, providing antioxidant capability. In addition, the incorporation of free radical-scavenging polyphenols into the cell membrane appear to enhance membrane activity, such as exchange of nutrients and wastes of the cellular environment. This also enhances cellular function and repair.

Methods and compositions of the present invention are particularly useful for treating damaged skin tissue, particularly various types of dermatitis, skin conditions such as rosacea, seborrhea, eczema (including severe hand and foot eczema presenting with skin fissures), xerosis (dry skin), psoriasis, thermal and radiation burns, and other types of inflammation. Polyphenol compositions of the invention are useful in treating both contact dermatitis, particularly diaper area dermatitis, and atopical dermatitis. Topical application of polyphenol according to the invention can also be effective to prevent symptoms in aging persons for the inhibition of microscarring of the dermis and to promote collagen production. It is an advantage of the invention that treatment or preventive measures employ, as an active ingredient, a natural compound found in edible olive oils. It is another advantage of the invention that topical application of these polyphenols provide a simple, non-invasive, nontoxic, over-the-counter topical method for treating all kinds of skin damage. Polyphenol can also be employed over primary irritants such as Retin-A™(tretinoin) application to counteract inflammation, and simultaneously enhance the effect of the other irritant (e.g., Retin-A™).

All references cited herein are hereby incorporated by reference, as are additional ingredients and methods set out in U.S. Pat. Nos. 4,775,530, 5,376,361, 5,409,693, 5,545,398, 5,574,063, 5,643,586, 5,709,868, 5,879,690, 5,965,618, and 5,968,618. Generally, these compositions contain other active ingredients summarized above that enhance the effect of active ingredients of the invention.

The above description is for the purpose of teaching the person of ordinary skill in the art how to practice the present invention, and it is not intended to detail all those obvious modifications and variations of it which will become apparent to the skilled worker upon reading the description. In one embodiment, the composition contains fromtion. It is intended, however, that all such obvious modifications and variations be included within the scope of the invention in any sequence which is effective to meet the objectives there intended, unless the context specifically indicates the contrary.

What is claimed is:

1. A method for the treatment of a skin condition selected from the group consisting of eczema, dermatitis, seborrhea, xerosis, rosacea, thermal or radiation burns, and psoriasis, comprising topically applying to affected skin areas a composition containing an effective amount of olive oil polyphenols selected from the group consisting of hydroxytyrosol, oleoeuropeine, and mixtures thereof.

2. A method according to claim 1 wherein the olive oil polyphenols are derived from olive oil.

3. A method according to claim 1 wherein the composition contains from about 0.1% to about 0.25% by weight polyphenol.

4. A method according to claim 1 wherein the composition comprises olive oil enriched with polyphenols.

5. A method according to claim 1 wherein the composition contains an α-hydroxy acid adjunct ingredient.

6. A method according to claim 5 wherein the α-hydroxy acid is glycolic acid.

7. A method according to claim 1 wherein the composition contains from about 0.1% to about 10% by weight polyphenol.

8. A method according to claim 7 wherein the composition contains from about 1% to about 7% by weight polyphenol.

9. A method according to claim 7 wherein the composition contains from about 2% to about 5% by weight polyphenol.

10. A method according to claim 1 wherein the polyphenol is hydroxy-tyrosol.

11. A method according to claim 1 wherein the polyphenol is oleuropein.

12. A method according to claim 1 wherein the polyphenol is a mixture of hydroxy-tyrosol and oleopeurine.

13. A method according to claim 1 wherein the skin condition is contact dermatitis.

14. A method according to claim 13 wherein the skin condition is diaper rash dermatitis.

15. A method according to claim 1 wherein the skin condition is atopic dermatitis.

16. A method according to claim 1 wherein the skin condition is eczema.

17. A method for the treatment of contact dermatitis comprising topically applying to affected skin areas a composition containing from about 0.1% to about 10% by weight olive oil polyphenols selected from the group consisting of hydroxytyrosol, oleoeuropeine, and mixtures thereof.

18. A method according to claim 17 wherein the contact dermatitis is diaper area dermatitis.

19. A method for the treatment of eczema comprising topically applying to affected skin areas a composition containing from about 0.1% to about 10% by weight olive oil poly-phenols selected from the group consisting of hydroxytyrosol, oleoeuropeine, and mixers thereof.

20. A method according to claim 19 wherein the composition contains from about 1% to about 7% polyphenols.

* * * * *